United States Patent [19]

Hanson et al.

[11] Patent Number: 5,281,391
[45] Date of Patent: * Jan. 25, 1994

[54] SYSTEM FOR DISINFECTING AND DISPOSING MEDICAL SHARPS

[75] Inventors: Leila Hanson; Joseph J. Hanson, both of Brookfield, Wis.

[73] Assignee: AvanTech Resource Center, Brookfield, Wis.

[ * ] Notice: The portion of the term of this patent subsequent to Dec. 21, 2110 has been disclaimed.

[21] Appl. No.: 836,629

[22] Filed: Feb. 13, 1992

[51] Int. Cl.⁵ .................................................. A61L 2/18
[52] U.S. Cl. ......................................... 422/25; 422/28; 422/32; 422/292; 422/300; 206/366; 206/370; 222/81; 383/202
[58] Field of Search .................... 422/25, 184, 292, 28, 422/29, 32, 300, 301, 294, 905; 206/370, 366; 220/23.86, 555, 909, 254, 336, 344, 214; 222/80, 81; 383/200, 201, 202; 606/151

[56] References Cited

U.S. PATENT DOCUMENTS

| | | | |
|---|---|---|---|
| 3,563,425 | 1/1969 | Clark | 222/478 |
| 3,774,822 | 11/1973 | Hazard | 222/541 |
| 3,811,604 | 5/1974 | Perry | 222/429 |
| 3,828,973 | 8/1974 | Birrell | 222/1 |
| 3,876,067 | 4/1975 | Schwarz | 206/366 X |
| 3,903,335 | 2/1976 | Jones | 427/361 |
| 3,937,323 | 2/1976 | Sagi et al. | 354/317 |
| 3,944,096 | 3/1976 | Eldrige, Jr. | 206/350 |
| 4,076,882 | 2/1978 | Fenster et al. | 428/215 |
| 4,080,615 | 3/1978 | Stella | 354/317 |
| 4,182,448 | 1/1980 | Huck et al. | 206/380 |
| 4,218,155 | 8/1980 | Weider | 401/132 |
| 4,321,999 | 3/1982 | Higgins | 206/370 |
| 4,626,971 | 12/1986 | Schultz | 206/366 X |
| 4,637,513 | 1/1987 | Eldrige, Jr. | 206/370 |
| 4,674,676 | 6/1987 | Sandel et al. | 229/142 |
| 4,754,898 | 5/1988 | Britt et al. | 222/487 |
| 4,793,483 | 12/1988 | Holmes | 206/438 x |
| 4,807,785 | 2/1989 | Pritchett | 222/442 |
| 4,842,138 | 6/1989 | Sandel et al. | 206/370 |
| 4,875,896 | 10/1989 | Kurtz | 604/187 |
| 4,886,165 | 12/1989 | Annett | 206/370 |
| 4,895,275 | 1/1990 | Quinn et al. | 222/81 |
| 4,900,500 | 2/1990 | Honeycutt | 264/263 |
| 4,921,491 | 5/1990 | Champ | 604/199 |

FOREIGN PATENT DOCUMENTS 3915194 1/1990 Fed. Rep. of Germany ...... 206/366

Primary Examiner—Robert J. Warden
Assistant Examiner—E. Leigh Dawson
Attorney, Agent, or Firm—Reinhart, Boerner, Van Deuren, Norris & Rieselbach

[57] ABSTRACT

A portable disinfecting and disposal device for medical waste. A disposal device includes a plastic container resistant to penetration, either from medical sharps inside or external effects. The device has a top and bottom portion with perimeter seal areas which upon closure prevent nondestructive reopening. The device top portion includes a chemically filled packet which is sealed during ongoing use for attachment of medical waste to the device but is unsealed by spikes for use after collection of the medical waste. The collected medical waste is accounted for by a system to identify the number and type of medical waste viewable through the plastic container after closing the device as well as when the device is open and being used.

20 Claims, 1 Drawing Sheet

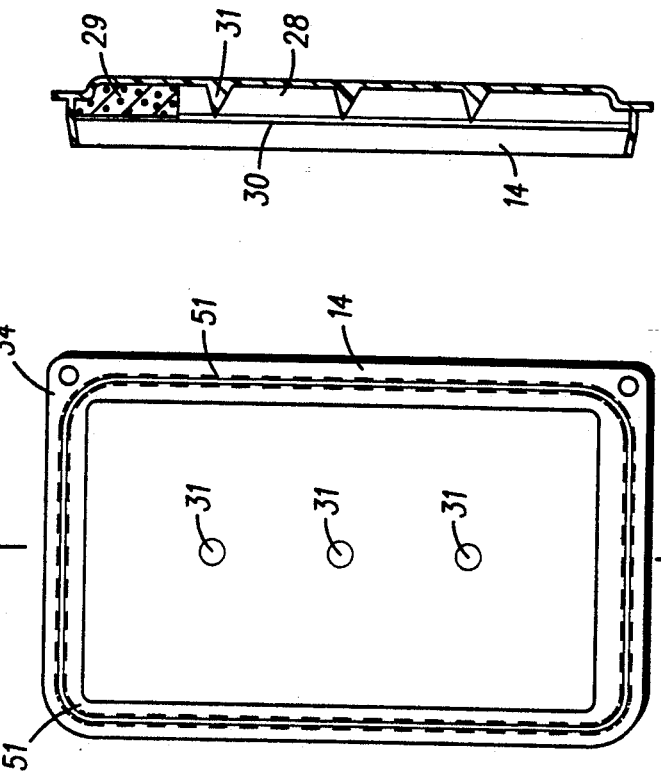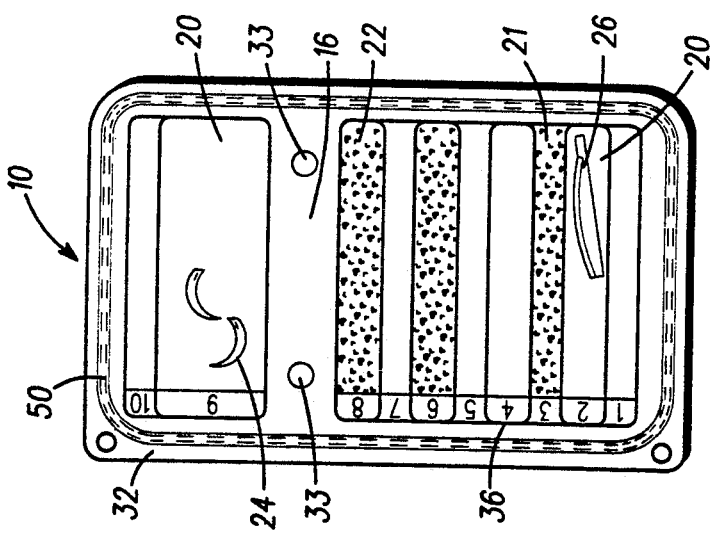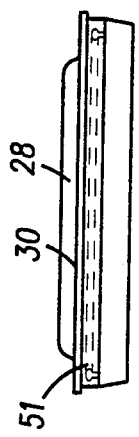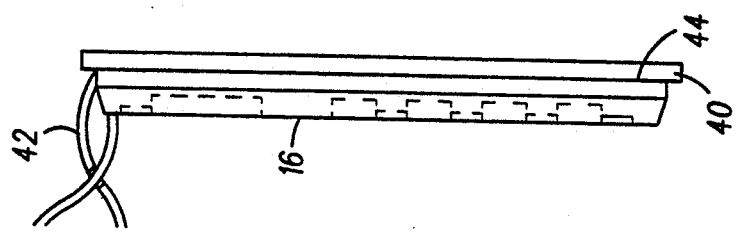

SYSTEM FOR DISINFECTING AND DISPOSING MEDICAL SHARPS

The present invention is generally with an improved method and device for the safe disposal of various surgical and other medical implements which are contaminated with biological media and other contaminated hazardous medical materials. More particularly, the invention is concerned with a new method and device for reliably insuring safe disposal of contaminated medical sharps while also disinfecting the contaminated sharps in the device at the immediate medical site where the medical procedures are taking place.

Devices for disposal of medical waste materials, including sharps used in surgical procedures, are commonly used in medical facilities. Such medical waste is considered hazardous waste and requires, by law (for example, OSHA regulations, state laws and regulations), the use of special handling and disposal procedures which are costly and inefficient. These laws however do little to alleviate a number of serious hazards to the environment and to the handlers of such waste materials, particularly at the site of the generation of the medical waste. Conventional disposer units co not normally allow for affirmatively neutralizing the biological hazard at the immediate medical site. Such hazards as contaminating bacteria and viruses remain intact and active in prior art devices after the waste materials are placed in the disposal device. Such devices therefore continue to harbor contaminated waste as the device is transported from the site of the medical procedure through the disposal system used by the medical institution and continuing through the external waste hauling system, if the medical institution does not have its own decontamination equipment. Only upon reaching a remote site is the biological contamination finally neutralized. The only currently available reasonable alternatives are on-site systems for large medical institutions which utilize complex, mass decontamination machinery for processing medical waste.

In addition, a number of current disposer devices do not affirmatively lock when closed, resulting in disposer containers being accidentally or intentionally reopened thereby exposing medical and waste disposal personnel to dangerous biological contaminants.

A number of currently used disposal devices are also easily penetrable, and ones which are made of heavy-gauge plastic have difficult to seal openings or the seal openings are easily defeated.

Further, a number of prior art disposal devices have low friction outer surfaces, causing sliding of the disposal device on the underlying surface during the medical procedure. This tendency to slide on a surgical tray or table further increases the hazard for health workers handling the sharps, potentially causing deadly contamination of the health care worker.

Medical waste disposal devices also usually do not allow visual inspection and counting of the enclosed sharps or waste materials after the device is closed. In addition, the devices do not include in combination an accounting means to ensure the number and type of medical waste included in a closed and sealed container.

Current medical waste disposal typically requires large treatment systems which involve complex operation, and such systems are nonportable and highly expensive. Such systems include autoclaving, incineration and bulk chemical treatment of the medical waste.

It is, therefore, an object of the invention to provide an improved portable disinfecting and disposal device for medical waste.

It is another object of the invention to provide a novel method of on site disinfecting and disposal of medical waste prior to removal from the immediate area of the medical procedure.

It is a further object of the invention to provide an improved method and device for disposing of medical waste while rendering the waste biologically harmless at the immediate site of the medical procedures.

It is an additional object of the invention to provide a novel method and device for reliably sealing disinfected medical waste in a container.

It is still another object of the invention to provide an improved method and device for disposing of disinfected medical waste accounting for the number and type of medical waste in the disposal container after it is sealed.

It is still a further object of the invention to provide a novel medical waste disposal container which has a nonskid bottom preventing unwanted sliding of the container.

It is yet a further object of the invention to provide an improved medical waste disposal container of substantially impenetrable plastic while allowing visual inspection of the waste material after the container is sealed.

Other objects and advantages of the invention, together with the manner of use and operation, will become apparent from the Detailed Description hereinafter and from the drawings described below:

BRIEF DESCRIPTION OF THE DRAWINGS

FIG. 1A illustrates a top view of a bottom portion of a medical waste disposal device constructed in accordance with the invention and FIG. 1AB shows the top portion thereof; FIG. 1B shows a side elevation view of the assembled device of FIG. 1AA; FIG. 1CA illustrates a front elevation view of the device view of FIG. 1AA, FIG. 1CB is a front elevation view of the device view of FIG. 1AB and FIG. 1D shows a cross section taken along 1D—1D in FIG. 1AB.

DETAILED DESCRIPTION OF PREFERRED EMBODIMENTS

A medical disposal device constructed in accordance with the invention is indicated generally at 10 in FIG. 1. The medical disposal device 10 (hereinafter, "the device 10") is preferably a plastic material which is highly resistant to penetration under normal medical system use in order to prevent the sharps or other medical waste from penetrating the device 10, either from the inside or from an outside source. The plastic can be any available material and necessary thickness which will provide the desired penetration protection, such as polyvinyl chloride, polystyrene, polyethylene, polypropylene, ethylene acrylic acid, Barex (a trademark of B. P. Chemical, Inc.) and combinations thereof. The plastic also is preferably highly resistant to environmental effects or chemical attack, either from the medical waste and disinfectant inside the device 10 or from exterior chemical attack.

In a preferred form of the invention, the device 10 has a top portion 14 (see FIG. 1AA) and a separate bottom portion 16 (see FIG. 1AB). In other forms of the invention the top portion 14 and the bottom portion 16 can be coupled by connecting means, such as a hinge integrally coupling the top portion 14 to the bottom portion 16.

The bottom portion 16 includes means for securely attaching medical waste, which can include medical sharps (such as, surgical needles, scalpels and hypodermic needles), biological tissue and also other medical devices, such as sponges, tubing, bandages and cloth implements. The means for securely attaching medical waste can include, for example, peel-covered peelable adhesive areas 20 or foam 21, or other fibrous areas 22 in FIG. 1A or contact cement and conventional viscous fluid media which tightly hold an object which contacts the media. Depending on the type of medical waste, the adhesive areas 20 or the foam or fibrous areas 22 are preferred means for securely attaching the medical waste. For example, surgical needles 24 are easily secured in either the adhesive areas 20 or the foam 21 or the fibrous areas 22, whereas scalpel blades 26 are secured best by the adhesive areas 20.

The device 10 further includes in the top portion a means for rendering harmless the medical waste, such as the surgical needles 24 attached to the adhesive areas 20. The means for rendering harmless is preferably a chemical to disinfect or sterilize the medical waste. A chemical could include, for example, a plastic packet 28 of commercial disinfectant or disinfectant soaked foam 29, such as hospital-level disinfectant as indicated in FIG. 1D. The plastic packet 28 is covered with a peel layer 30. When the peel layer 30 is removed, the plastic packet 28 is ready for use. In this form of the invention the top portion 14 see FIG. 1AB can include coupled means such as spikes 31 (or 33 in the bottom portion 16 shown in FIG. 1AA) to penetrate the plastic packet 28 to release disinfectant trapped beneath the sealed peel layer 30 (or to release disinfectant in the foam 29 in the bottom portion 16).

In a most preferred embodiment the means for attaching medical waste is constructed of a material which allows percolation of a liquid or gaseous disinfectant through the attaching means. The disinfectant is therefore able to contact the attached medical waste and neutralize the biological contaminants associated with the medical waste.

When the user has disposed of the medical waste in the device 10 in the manner described above, a seal means is utilized in order to sealingly close the device 10. In particular, the seal means preferably acts to close the device 10 to prevent reopening the closed device 10. As shown in FIG. 1AA and FIG. 1AB a respectively in 1CA and 1CB a preferred embodiment comprises a recessed channel 50 the bottom portion 16 and a protruding ridge 51 on the top portion 14. The recessed channel 50 matingly receives the ridge 51, and the shapes of the channel 50 and ridge 51 are designed to sealingly close the device 10 and also nondestructive reopening of the device 10. The particular shape of the channel 50 and the ridge 51 can be, for example, keyway design or other locking mechanism which allows easy entry of the ridge 51 into the channel 50 but preventing nondestructive removal of the ridge 31 from the channel 50 for example, the cross sectional view in FIG. 1CA and CB of the ridge 51 and mating channel 50).

In another form of the invention, the seal means can be, a first and second seal means, such as, conventionally peelable seal areas 32 and 34, respectively, shown in FIG. 1AA and 1AB. Other possible sealing means for the device 10 can be areas of contact cement, viscous fluid media, or thermally activated cement. In addition, the sealing means can be an epoxy formula wherein a viscous hardener portion is on the seal area of the top portion 14 and a viscous epoxy resin portion is on the seal area of the bottom portion 16.

Additional chemical means for rendering harmless the medical waste can include, for example, gaseous materials and acids which preferentially react with biological materials and/or disinfectants or sterilizing chemicals specific to selected viruses and/or bacteria. Once the device 10 is sealed and the chemical disinfection and/or sterilization is complete, the device 10 containing the decontaminated medical wastes can be more easily disposed of. An advantage of the device 10 is that the disposal standards are substantially more demanding and costly for disposal devices containing active harmful biological contaminants, compared to the deactivated contents in the device 10 of the invention.

The invention shown in FIG. 1AA includes accounting means for numbering and identifying the medical waste contained in the device 10. There is shown a sequential numbering of each individual area 36 which retains one of the medical wastes. In other forms of the accounting means, different size areas can be used to attach medical waste. The actual numbering can be effectuated by numbers imprinted on the housing of the device 10 as shown in FIG. 1AA.

Another feature of the invention is the ability to firmly fix the position of the device 10 onto a holding table or other surface 40 shown in FIG. 1B. This can be accomplished using pincers 42 or gripping surface 44 coupled to the bottom of the bottom of the bottom portion 16. The pincers 42 are passed through the edge of the bottom portion 16 into the surface 40.

Previous medical disposal systems suffer from a variety of problems. Rigorous health and environmental laws and regulations require extensive precautions be followed and expensive procedures implemented in order to dispose of biologically active medical waste. The instant invention overcomes a number of disadvantages of the prior art in a combination of a portable disposal device which reliably disinfects and retains the neutralized medical waste, while rendering harmless the medical waste at the local site of the medical procedures. The device also resists penetration of the housing and allows visual inspection of the sealed contents. The device 10 is also highly portable, combining the ability to reliably affix medical sharps and other such waste to the device, while simultaneously allowing disinfection of the medical sharps. In addition, the seal design avoids accidental opening or reuse. The resulting combination of features provides a simple, effective system which allows neutralizing of the biological contamination early in the waste disposal process. The system does not demand performance of expensive and unnecessary procedures. The system further allows accurate accounting for the specific medical wastes and thus ensures categorization as less hazardous waste. Many prior art systems allow unaccounted mixing of different types of medical waste and of unknown quantities. Such systems do not allow reliable classification as wastes of known types and number and therefore must be treated as the worst possible case.

While preferred embodiments of the invention have been shown and described, it will be clear to those skilled in the art that various changes and modifications can be made without departing from the invention in its broader aspects as set forth in the claims provided hereinafter.

We claim:

1. A portable disinfecting and disposal device for medical waste comprising:
   a plastic-container for receiving medical waste and a couplable top portion and bottom portion, said top portion including first seal means and said bottom portion including second seal means for sealing said top and bottom portions together;
   said bottom portion further including means for securely attaching said medical waste thereto; and
   said top portion further including means for disinfecting said medical waste attached to said bottom portion with said disinfecting means sealed until the user unseals and exposes said disinfecting means and the user is able to join said first and second seal means to close said device, thereby sealing in said disinfecting means and said medical waste at the local site of the medical procedure.

2. The disposal device as set forth in claim 1 wherein said plastic container is constructed of plastic resistant to penetration during use and disposal.

3. The disposal device as defined in claim 2 further including means for nonremovably connecting together said top and bottom portion.

4. The disposal device as defined in claim 3 wherein said connecting means comprises a mating channel and ridge, respectively, on said top and bottom portions.

5. The disposal device as defined in claim 4 wherein said disinfecting means comprises a liquid disinfectant and said first and second seal means, when coupled, form a leak proof seal for said disinfectant.

6. The disposal device as set forth in claim 2 wherein said plastic is selcted from the group consisting essentially of polyvinyl chloride, polystyrene, polyethylene, polypropylene, ethylene acrylic acid, Barex® and combinations thereof.

7. The disposal device as defined in claim 1 wherein said seal means comprise a channel and mating ridge on said bottom and top portions, respectively.

8. The disposal device as defined in claim 1 wherein said means for disinfecting comprises a chemical for at least disinfecting said medical waste.

9. The disposal device as defined in claim 8 wherein said chemical comprises at least one of a plastic packet and a foam material containing a disinfectant.

10. The disposal device as defined in claim 1 further including an identifying means coupled to said disposal device for numbering and identifying said medical waste.

11. The disposal device as defined in claim 1 further including a pincer device coupled to said disposal device for attaching said disposal device to a selected surface.

12. The disposal device as defined in claim 1 wherein said means for securely attaching comprises at least one of a foam and a peelable adhesive area.

13. The disposal device as defined in claim 1 wherein said means for securely attaching comprises at least one of a foam or fibrous area coupled to said bottom portion.

14. The disposal device as defined in claim 1 further including identifying means imprinted on said top and/or said bottom portions having said medical waste attached thereto.

15. The disposal device as defined in claim 12 further including a nonskid surface element disposed on the outside surface of said device.

16. A portable disinfecting and disposal device capable of holding medical waste and/or medical sharps, comprising:
   a plastic-container having a top portion and a bottom portion, said top portion including a first seal means along the entire perimeter thereof and said bottom portion including a second seal means for matingly sealing to said first seal means and said top and bottom portions couplable by connecting means;
   said bottom portion further including means for securely attaching thereto medical sharps and for holding medical waste;
   said top portion further including means for disinfecting said medical waste and/or medical sharps when said top portion is attached to said bottom portion with said means for disinfecting sealed until unsealed by the user of said device causing release of disinfectant and the user joining said first and second seal means to close said device, thereby sealing in said disinfectant and disinfecting said medical waste and/or medical sharps; and
   accounting means coupled to said disposal device for numbering and identifying said medical waste and/or medical sharps attached to said disposal device.

17. The disposal device as defined in claim 16 wherein said connecting means comprises a nonleaking sealing element.

18. The disposal device as defined in claim 16 further including nonskid gripping areas disposed on one of the exterior contact surfaces of said device.

19. The disposal device as defined in claim 16 further including spikes for opening said disinfecting means.

20. A method of rendering harmless and disposing medical waste, comprising the steps of:
   providing a portable disposal device comprised of a plastic container having a top portion and a bottom portion, said top portion including a first seal means and said bottom portion including a second seal means for matingly sealing to said first seal means to form a nonreopenable closure and said bottom portion further including means for securely attaching medical waste to said bottom portion and said top portion further including means for disinfecting said medical waste attachable to said means for securely attaching;
   attaching said medical waste to said means for securely attaching;
   opening said means for disinfecting said medical waste to release disinfectant when the suer is ready to close said plastic container at the local site of the medical procedure; and
   closing said plastic container to matingly seal said first and second seal means to one another, thereby nonreopenably sealing in said disinfectant enabling the disinfecting of said medical waste.

* * * * *